United States Patent [19]

Astheimer et al.

[11] Patent Number: 4,707,605

[45] Date of Patent: Nov. 17, 1987

[54] METHOD AND APPARATUS FOR THERMAL EXAMINATION OF A TARGET BY SELECTIVE SAMPLING

[75] Inventors: Robert W. Astheimer, Westport; William J. Kelly, Bridgeport, both of Conn.

[73] Assignee: Barnes Engineering Company, Shelton, Conn.

[21] Appl. No.: 860,512

[22] Filed: May 7, 1986

[51] Int. Cl.$^4$ .................. G01N 21/62; G02B 6/00
[52] U.S. Cl. .................. 250/347; 250/340; 250/341; 250/353
[58] Field of Search .............. 250/341, 340, 348, 347, 250/353, 227; 350/96.29; 356/6.3

[56] References Cited

U.S. PATENT DOCUMENTS

| | | | |
|---|---|---|---|
| 3,566,120 | 2/1971 | Lane, Jr. ..................... | 250/341 X |
| 4,427,881 | 1/1984 | Ruell ............................ | 250/227 |
| 4,481,418 | 11/1984 | Vanzetti et al. ............ | 250/338 |
| 4,533,834 | 8/1985 | McCormack ................ | 250/554 |
| 4,547,666 | 10/1985 | Heal ............................. | 250/227 |

FOREIGN PATENT DOCUMENTS 2570819  3/1986  France .................. 250/353

Primary Examiner—Constantine Hannaher
Attorney, Agent, or Firm—Parmelee, Bollinger & Bramblett

[57] ABSTRACT

Selective thermal examination of a target is provided by scanning the field of view of an infrared detector over predetermined areas of a target. The selection is made by a plurality of infrared fibers having first and second ends with the first ends being stationarily mounted in a fixed array suitable for being scanned by the detector or a detector coupled to each first end which are electrically scanned, while the second ends of the infrared fibers are directed by the user to selected areas of the target which are desired to be thermally examined. The infrared detector or detectors are then scanned over the first ends of the infrared fibers in the fixed array for sequentially thermally examining the selected areas of the target. The selected areas may be changed simply by rearranging and redirecting the second ends of the infrared fibers with respect to the target areas desired to be examined.

5 Claims, 7 Drawing Figures

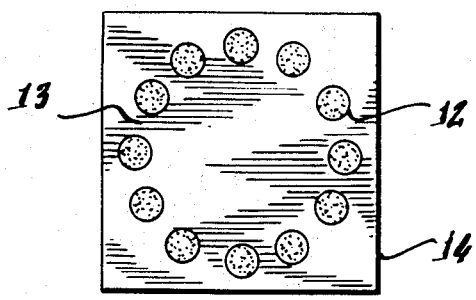
Fig. 1.
Fig. 2.
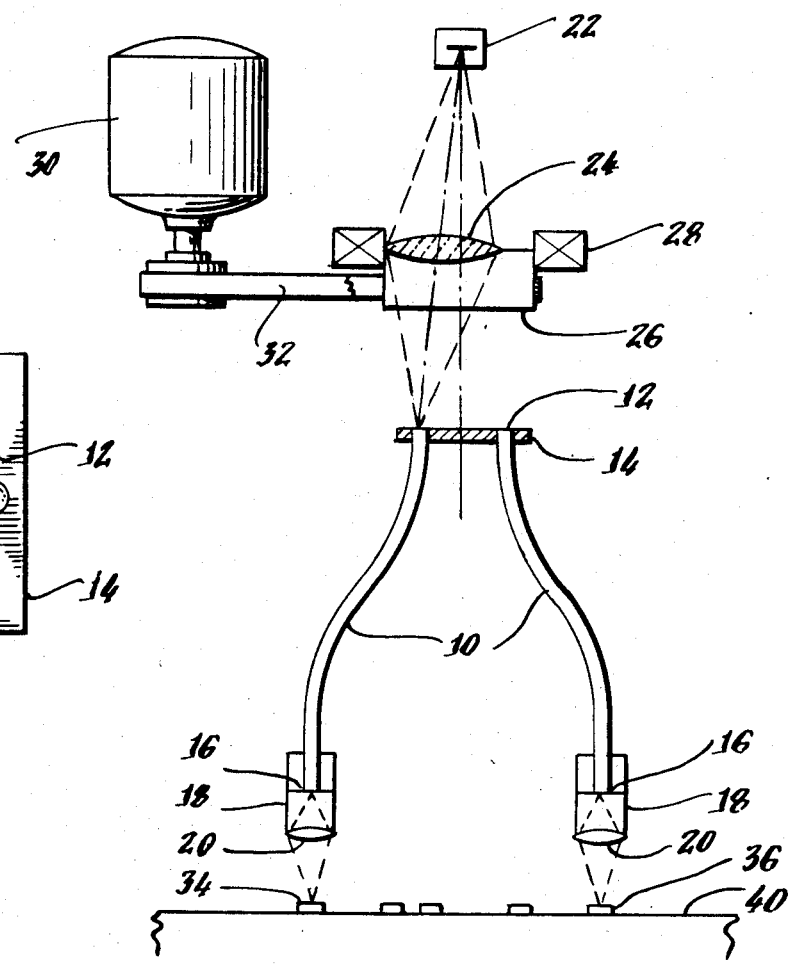
Fig. 4.
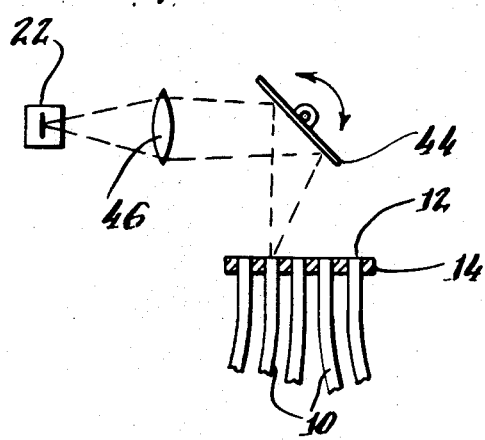
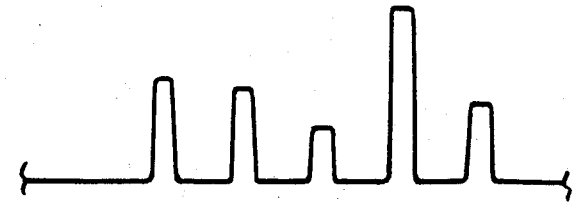
Fig. 3.
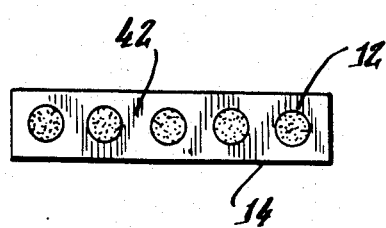
Fig. 5

METHOD AND APPARATUS FOR THERMAL EXAMINATION OF A TARGET BY SELECTIVE SAMPLING

BACKGROUND OF THE INVENTION

This invention relates to the infrared non-destructive testing of targets and more particularly, to a method and apparatus for the thermal examination of a target by selective sampling utilizing an infrared fiber optic radiometer.

Infrared scanners have been utilized for non-destructively destructively thermally testing a variety of products and uses, such as machines, printed circuits, chips, microcircuits, process control, etc. However, many of the infrared scanners are research type instruments which have predetermined scanning patterns for monitoring predetermined areas of the product and therefor are too slow for on line inspecting of mass production items. However, for such purposes it is not always necessary to thermally survey the entire area or every point on a product, circuit, or device. In many cases the selection of a few significant elements for thermally sensitive areas for example, 5-20 may be all that is required. Any apparatus utilized for such a purpose must have the capability of selectively changing the significant areas to be examined without substantially structurally changing the infrared radiometer which is being utilized for the examination otherwise a new instrument would have to be used whenever the selection of desired areas is changed or single individual measurements would have to be made for each of the points of interest.

SUMMARY OF THE INVENTION

Accordingly, it is an object of this invention to provide a new and improved method and apparatus for the thermal examination of a target by selective sampling in which the selective sampling may be changed readily by the user without substantially altering the apparatus being employed for the thermal examination.

A further object of this invention is to provide a new and improved method and apparatus for the thermal examination of a target utilizing a scanning infrared radiometer in which the scanning is not changed even though the areas of the target being sampled have been changed.

In carrying out this invention in one illustrative embodiment therein, a method and apparatus are provided for the selective thermal examination of a target which apparatus includes an infrared detector and a plurality of infrared fibers having first and second ends. The first ends of the infrared fibers are mounted in a fixed array suitable for being optically or electrically scanned by the infrared detector(s) while the second ends of the fibers are directed to selective areas of a target which are desired to be thermally examined by the infrared detector. Scan means are provided for scanning the infrared detector(s) over the first ends of the infrared fibers in the fixed array, whereby the selected areas of the targets established by the second ends of the infrared fibers, are thermally examined by the infrared detector(s). The first ends of the infrared fibers may be fixed in a circular or a linear fashion with scanning means being provided for scanning the detector(s) in a circular or a linear pattern, respectively. The method of examination permits changing the areas being examined by the infrared detector(s) by merely changing where the second ends of the fibers are pointed without changing the positions of the first ends of the fibers or the remainder of the apparatus.

Among the many advantages of the new method and apparatus for the thermal examination of the target by selective sampling is the use of the same fiber optic infrared radiometer whose structure does not have to be altered, for scanning different areas of a sample. The apparatus may be utilized with different targets whose significant areas of examination may be different without essentially altering the structure of the examination apparatus.

BRIEF DESCRIPTION OF THE DRAWINGS

The invention, together with further objects, features, advantages and aspects thereof will be more clearly understood by reference to the following description taken in connection with the accompanying drawings, in which:

FIG. 1 illustrates one embodiment of the fiber optic infrared radiometer which may be utilized in accordance with the present invention;

FIG. 2 is a top view illustrating the first ends of infrared fibers being mounted in a fixed array suitable for scanning by the apparatus shown in FIG. 1;

FIG. 3 illustrates a signal produced by the scanning of fibers illustrated in FIg. 1;

FIG. 4 is a partial view of another embodiment of a fiber optic infrared radiometer utilizing a linear scanning arrangement in accordance with the present invention; and FIG. 5 is a top view of the first end of the infrared fibers being mounted in a fixed array suitable for being scanned in a manner illustrated in FIG. 4.

DESCRIPTION OF THE PREFERRED EMBODIMENTS

Figure 6:
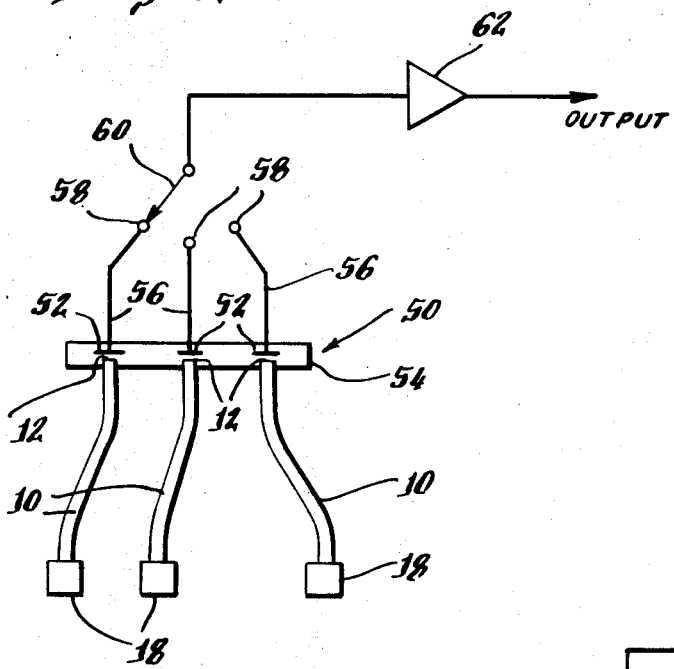
FIG. 6 illustrates a partial schematic diagram of another embodiment of a fiber optic infrared radiometer employing electrical scanning.

Referring now to FIG. 1, a plurality of infrared transmitting fibers 10 have first ends 12 mounted in a stationary fixture 14 and second ends 16 positioned in end caps 18 each of which carries an objective lens 20. The movable second ends 16 of the fibers 10 do not require the lenses 20 if the second ends 16 can be placed close enough to the object being thermally examined. The infrared fibers 10 will have ground and polished ends with accompanying sheaths. The type of infrared fibers utilized will depend on the particular application and the transmission characteristics of that fiber. As an illustrative example IR fibers of chalcogenide glass which transmits infrared radiation from 6-14 microns indentified as model IRLG, made by Gallileo Electro Optics Corporation of Sturbridge, Mass. having a diameter of 0.3 mm may be suitable for semiconductor inspection. The type of infrared fiber as well as its diameter, as has been pointed out, will depend on the application to which the thermal examination is applied.

In the embodiment of FIG. 1, the first ends 12 of the infrared fibers 10 are mounted in a fixed circular array 13 as is diagrammatically illustrated in FIG. 2. The fiber array 13 may be fixedly potted in a circle in a mount 14, or the mount 14 may be formed of a mesh in which the ends 12 may be fixedly mounted therein with the polished ends 12 protruding upwardly therefrom. The fixed fiber array 13 is adapted to be optically scanned by an infrared detector 22, for example, a pyroelectric detector. Different types of infrared detectors may be utilized depending on the application and the sensitivity required and in a preferred embodiment involving electrical scanning illustrated in FIG. 6 pyroelectric detectors are used. The infrared detector 22 is scanned over the fixed circular array 13 by a rotating eccentrically mounted lens 24 carried in a rotatable housing 26 in bearings 28. The rotating housing 26 is driven by a motor 30 via a pulley 32. The rotating eccentrically mounted lens 24 causes the infrared detector 22 to scan a circle at 30 rps which circle coincides with the circular fixed array 13 of the infrared fibers 10.

The other or second end 16 of fibers 10 with the lenses 20 attached when required are directed at specific target areas 34 and 36 on a target 40 which could be a printed circuit, micro-circuit, semi-conductor device or other component or apparatus which is desired to be thermally inspected. Although only two fibers 10 have been illustrated examining points 34 and 36 on the target 40, it will be appreciated that many more are contemplated for example, 5–20 depending on the type of target and the size of the apparatus as well as the type of application involved. Accordingly, rotation of the eccentrically mounted lens 24 causes the detector 22 to sequentially sample the infrared fiber 10 out-puts. FIG. 3 illustrates the type of output from the infrared detector 22 in response to scanning the detector over elemental areas such as 34 and 36 on the target 40. The higher amplitude signals which are generated indicate a higher relative temperature.

Different areas or points on the target 40 may be examined by utilizing the same apparatus with the fiber 10 ends 12 mounted as shown merely by changing the position of the end caps 18 and directing the ends 16 of the fibers 10 to different elemental areas on the target 40. Thus, the apparatus is not changed, only the location of the second end 16 of the fibers 10. Additionally, if fewer area are desired to be examined, the second ends 16 or the lenses 20 when used on the second ends 16 of the fibers not being used may be covered or simply directed at ambient targets.

FIGS. 4 and 5 illustrate another embodiment employing a different scanning arrangement for the method applied in the present invention. In this embodiment, the first ends 12 of the infrared fibers 10 are mounted in the scanning fixture 14 in a linear array 42 as illustrated in FIG. 5. The linear array 42 is scanned by an oscillating scanning mirror 44 which scans the detector 22 through its objective lens 44 on the first ends 12 of the IR fiber optics 10 arranged in the linear array 42 in the fixture 14. This approach provides a simpler scanning mechanism but may not allow for the scanning of a larger number of elements formed by the circular array 13. This may be corrected, however, by providing more than one spaced linear array which may be scanned by the scanning mirror 44 which may be indexed vertically for accomodating more than one row. If too many rows are provided such a scanning arrangement may ultimately suffer the disadvantages of those research scanning instruments which cover the entire surface of the target. As in the embodiment 12 of FIG. 1, the second ends 16 of the infrared fibers 10 are directed to the specific areas of the target 40 which are desired to be examined. As in the former embodiment, the second ends 16 may be redirected for different applications or for examining different areas of the same target without varying the rest of the structure.

In a preferred embodiment, the same general method of thermal examination is employed using electrical instead of optical detector scanning. As is illustrated in one form in FIG. 6, an infrared detector array, referred to generally with the reference numeral 50, comprises a plurality of individual infrared detector elements 52, preferably pyroelectric detectors, which may be fabricated individually or in array. The pyroelectric detectors 52 may be mounted on a substrate 54 with the ends 12 of the IR fibers 10 positioned in the substrate in communication with a detector element 52. Alternatively, the detector elements 52 may be mounted on the ends 12 of the fibers 10 and positioned in any suitable holders. The detector elements are electrically connected by leads 56 to contacts 58 of a commutator switch 60. Accordingly, the commutator switch 60 samples the output of each detector element 52 in the detector array 50. The switch 60 is coupled to an amplifier 62 whose output may be applied to a suitable display and/or use in a process control function, for example, to remove the product from the production line if the temperature exceeds a predetermined level, etc. The type of infrared detectors utilized will again depend on the application. The commutator switch 60 is preferably a solid state switch, e.g. Mosfets, for electrically sampling the radiant output of the first ends of the infrared fibers.

Figure 7:
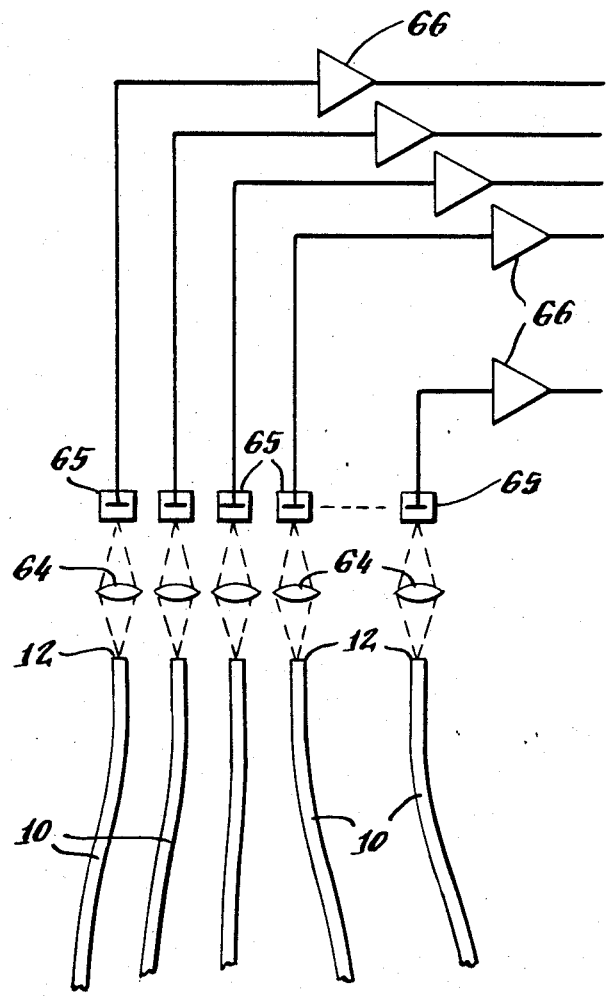
FIG. 7 is a schematic diagram of another embodiment of the invention.

In the embodiment illustrated in FIG. 7 an infrared detector 65 is coupled to each of the first ends 12 of the infrared fibers 10. This coupling is illustrated using lenses 64. If the detectors can be positioned close to the ends 12 the lenses 64 may not be required. Each of the detectors 65 is connected to an amplifier 66 with the outputs therefrom being applied to displays, recorders and/or utilization circuits such as process control devices. This circuit arrangement provides continuous thermal monitoring of the selected areas of the target at which the second ends of the IR fibers are directed.

Since other changes and modifications varied to fit particular operating requirements and environments will be apparent to those skilled in the art, the invention is not considered limited to the examples chosen for purposes of illustration, and includes all changes and modifications which do not constitute a departure from the true spirit and scope of this invention as claimed in the following claims and equivalents thereto.

What is claimed is:

1. Apparatus for the selective thermal examination of a target with the areas of examination being selectable by the user comprising:
   an infrared detector means,
   a plurality of infrared fibers having first and second ends,
   said second ends being movable and directed by the user to selective areas of a target which are desired to be thermally examined by said infrared detector means,
   means for mounting said first ends of said infrared fibers in a fixed array suitable for being scanned by said infrared detector means, and
   the individual second ends of said fibers are aimed and directed by the user at the areas of the target to be examined,
   optical scan means for scanning said infrared detector means over said first ends of said infrared fibers in said fixed array such that the selected areas of said target as established by the aiming of said second ends of said infrared fibers by the user are thermally examined by said infrared detector means.

2. The apparatus as claimed in claim 1 wherein said second ends of said infrared fibers have objective lenses associated therewith for imaging said second ends of said infrared fibers positioned by the user on the areas of said target which are desired to be examined.

3. The apparatus as claimed in claim 1 in which said first ends of said infrared fibers are arranged in a circular fixed array and said scan means comprises a rotating optical element which causes said infrared detector means to scan said circular fixed array.

4. The apparatus as claimed in claim 1 in which said first ends of said infrared fibers are arranged in fixed linear arrays and said scanning means comprises an oscillating scanning mirror which causes said infrared detector means to be scanned over said fixed linear arrays.

5. A method of non-destructive thermal examination of a target which enables the user to selectively choose and change the areas of the target which are desired to be examined comprising the steps of:

mounting the first ends of a plurality of infrared fibers in a fixed pattern capable of being optically scanned, selectively directing the second ends of the plurality of infrared fibers to view a plurality of different locations on a target which is being examined in accordance with the desires of the user, scanning the first ends of said infrared fibers in said fixed pattern and detecting the infrared outputs from each of said first ends of said infrared fibers such that said different locations on said target determined in accordance with the positioning of the second ends of said infrared fibers with respect to said target are thermally examined, changing the positioning of the second ends of said infrared fibers with respect to said target for thermally examining different locations on said target without changing the scanning pattern.

* * * * *